United States Patent [19]

Berger et al.

[11] Patent Number: 5,492,914
[45] Date of Patent: Feb. 20, 1996

[54] 2-(1-AZABICYCLO[2.2.2]OCT-3 S-YL)-6-HYDROXY-2,4,5,6-TETRAHYDRO-1H-BENZ[DE]ISOQUINOLIN-1-ONE AND 2-(1-AZABICYCLO[2.2.2]OCT-3'S-YL)-6-HYDROXY-2,3,3A,4,5,6-HEXAHYDRO-1H-BENZ [DE]ISOQUINOLIN-1-ONE AND INDIVIDUAL STEREOISOMERS THEREOF

[75] Inventors: Jacob Berger, Los Altos Hills; Robin D. Clark, Palo Alto; Paul E. Weller, Mountain View; Douglas L. Wren, Palo Alto, all of Calif.

[73] Assignee: Syntex (U.S.A.) Inc., Palo Alto, Calif.

[21] Appl. No.: 282,110

[22] Filed: Jul. 28, 1994

[51] Int. Cl.[6] .................. A61K 31/485; C07D 401/08
[52] U.S. Cl. .............................. 514/296; 546/99
[58] Field of Search ............................. 546/99; 514/296

[56] References Cited

U.S. PATENT DOCUMENTS 5,202,333  4/1993  Berger .................... 514/296

FOREIGN PATENT DOCUMENTS

WO93/22310  11/1993  WIPO .

OTHER PUBLICATIONS

Clark RD. et al. J. Med. Chem. (1993) 36, 2645–2657.

*Primary Examiner*—C. Warren Ivy
*Assistant Examiner*—Evelyn Huang
*Attorney, Agent, or Firm*—Wayne W. Montgomery

[57] ABSTRACT

This invention relates to 2-(1'-azabicyclo[2.2.2]oct-3'S-yl)-6-hydroxy-2,4,5,6-tetrahydro-1H-benz[de]isoquinolin-1-one and 2-(1'-azabicyclo[2.2.2]oct-3'S-yl)-6-hydroxy-2,3,3a,4,5,6-hexahydro-1H-benz[de]isoquinolin-1-one and their individual stereoisomers and uses and the processes for their making.

23 Claims, No Drawings

2-(1-AZABICYCLO[2.2.2]OCT-3S-YL)-6-HYDROXY-2,4,5,6-TETRAHYDRO-1H-BENZ[DE]ISOQUINOLIN-1-ONE AND 2-(1-AZABICYCLO[2.2.2]OCT-3'S-YL)-6-HYDROXY-2,3,3A,4,5,6-HEXAHYDRO-1H-BENZ[DE]ISOQUINOLIN-1-ONE AND INDIVIDUAL STEREOISOMERS THEREOF

BACKGROUND OF THE INVENTION

1. Field of the Invention

This invention relates to 2-(1'-azabicyclo[2.2.2]oct-3'S-yl)-6-hydroxy-2,4,5,6-tetrahydro- 1-H-benz[de]isoquinolin-1-one and 2-(1'-azabicyclo[2.2.2]oct-3'S-yl)-6-hydroxy-2,3,3a,4,5,6-hexahydro-1H-benz[de] isoquinolin-1-one and their individual stereoisomers and uses and the processes for their making.

2. Description of the Invention

Serotonin, a neurotransmitter with mixed and complex pharmacological characteristics, was first discovered in 1948 and subsequently has been the subject of substantial research. Serotonin, also referred to as 5-hydroxytryptamine (5-HT), acts both centrally and peripherally on discrete 5-HT receptors. The 5-HT receptor is presently delineated into four major subclassifications—5-HT$_1$, 5-HT$_2$, 5-HT$_3$ and 5-HT$_4$ receptors—each of which may also be heterogeneous. Receptors of the 5-HT$_3$ subclass pervade autonomic neurons and appear to regulate the release of a variety of neurotransmitters in the gastrointestinal, cardiovascular and central nervous systems.

5-HT$_3$ receptors are located in high densities on neurons associated with the emetic reflex and drugs which block the interactions of serotonin at the 5-HT$_3$ receptor level, i.e., 5-HT$_3$ receptor antagonists, possess potent antiemetic properties. Such antagonists demonstrate utility for counteracting the emetic effects of cancer chemotherapy and radiotherapy (see Drugs Acting on 5-Hydroxytryptamine Receptores: *The Lancet* Sep. 23, 1989 and references cited therein).

Functional bowel disorders are prevalent in much of the industrialized world. Chronic gastroesophageal reflux disease alone may be present in as much as 15% of the population. Use of prokinetic agents is one of the most effective methods known for treating such disorders. Because many 5-HT$_3$ antagonists possess prokinetic properties and are relatively free form side effects they are particularly useful in the treatment of gastrointestinal disease (see Reynolds R. C. Prokinetic Agents: A Key in the Future of Gastroenterology. *Gastroenterology Clinics of North America* 1989; 18:437–457).

5-HT$_3$ receptors are present in those areas of the brain which control mood, emotion, reward and memory. 5-HT$_3$ receptor antagonists reduce mesolimbic dopamine levels, a necessary property for antipsychotic activity. Such antagonists also increase cholinergic tone in the limbic-cortical region, which may explain their cognitive enhancing effects. In addition, 5-HT$_3$ antagonists possess anxiolytic properties, demonstrate potential for use in the treatment of dependency disorders and are under investigation in patients with schizophrenia (see article from *The Lancet* previously cited).

There is evidence that 5-HT$_3$ receptors mediate nociceptive input to afferent neurons (see Glaum, S., Proudfit, H. K., and Anderson, E. G.; *Neurosci. Lett.* 1988; 95:313). 5-HT$_3$ antagonists may therefore be of value in the control of pain, particularly migraine (see Peatfield R.; Drugs and the Treatment of Migraine. *Trends Pharmacol. Sci.* 1988; 9:141).

The 5-HT$_3$ receptor antagonist ICS 205–930 inhibits arrhythmias in a variety of animal models and exerts mixed class III and class I antiarrhythmic properties in ventricular myocytes (see Schlltysik, G. Imoto, Y., Yatani, A. and Brown, A. M.; *J. Pharmacol. Exp. Ther.* 1988; 245:773 and references therein). 5-HT$_3$ antagonists may therefore be of use in treating or preventing arrhythmias.

U.S. Pat. No. 5,202,333 describes certain tricyclic compounds with 5-HT$_3$ receptor antagonist properties. Included among the tricyclic 5-HT$_3$ receptor antagonists described in U.S. Pat. No. 5,202,333 are (1-azabicyclo[2.2.2]oct-3S-yl)-2,3,3a,4,5,6-hexahydro-1H-benz[de]isoquinolin-1-one and 2-(1-azabicyclo[2.2.2]oct-3S-yl)-2,4,5,6-tetrahydro-1H-benz[de]isoquinolin-1-one and it is now known that 2-(1-azabicyclo[2.2.2]oct-3S-yl)-6-hydroxy-2,3,3a,4,5,6-hexahydro-1H-benz[de] isoquinoline-1-one and 2-(1-azabicyclo[2.2.2]oct-3S-yl)-6-hydroxy-2,4,5,6-tetrahydro-1H-benz[de]isoquinolin- 1-one, respectively, are human metabolites thereof.

SUMMARY OF THE INVENTION

This invention relates to a compound of Formula I:

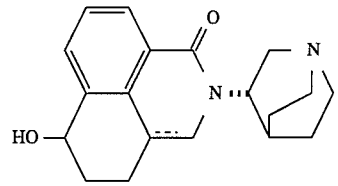

in which the dashed line denotes an optional double bond; and the pharmaceutically acceptable salts, individual stereoisomers, mixtures of stereoisomers, N-oxide derivatives and O-β-D-glucuronide conjugates thereof.

A second aspect of this invention is a pharmaceutical composition comprising a therapeutically effective amount of a compound of Formula I, or of an individual isomer, a mixture of isomers, or a pharmaceutically acceptable salt or salts or an N-oxide derivative thereof, in combination with one or more pharmaceutically acceptable excipients.

A third aspect of this invention is a method for treating a disease involving emesis, gastrointestinal disorders, CNS disorders, cardiovascular disorders or pain by administering a therapeutically effective amount of a compound of Formula I or a pharmaceutically acceptable salt or salts, individual stereoisomer, mixture of stereoisomers, N-oxide derivative or O-β-D-glucuronide conjugate thereof.

A fourth aspect of this invention is the processes for preparing compounds of Formula I and is set forth in "Detailed Description of the Invention".

DETAILED DESCRIPTION OF THE INVENTION

Definitions

As used herein:

"Leaving group" has the meaning conventionally associated with it in synthetic organic chemistry, i.e., an atom or group displaceable under alkylating conditions, and includes hydroxy, halo, (C$_{1-4}$)alkoxy (e.g., methoxy, ethoxy and the like), aryloxy (e.g., phenoxy and the like), (C$_{1-4}$)alkylthio (e.g., methylthio, ethylthio and the like), arylthio (e.g., phenylthio and the like) and alkane- or arenesulfonyloxy (e.g., mesyloxy, ethanesulfonyloxy, benzenesulfonyloxy, trifluoromethanesufonyloxy, tosyloxy and the like).

"Halo" means fluoro, chloro, bromo, or iodo.

"Protective group" has the meaning conventionally associated with it in synthetic organic chemistry, i.e., a group which selectively blocks one reactive site in a multifunctional compound such that a chemical reaction can be carried out selectively at another unprotected reactive site. Certain processes of this invention rely upon protective groups to block reactive hydroxy groups present in the reactants. Acceptable hydroxy protecting groups include substituted methyl (e.g., methoxymethyl, methythiomethyl, benzyloxymethyl, tert-butoxymethyl, benzyl, etc.), substituted ethyl (e.g., 1-ethoxyethyl, 1-methyl-1-methoxyethyl, etc.), silyl (e.g., trimethylsilyl, triethylsilyl, tert-butyldiphenylsilyl, etc.) and the like.

"Deprotection" is the process by which a protective group is removed after the selective reaction is completed to give the desired unprotected product in reasonable yield.

"Animal" includes humans, non-human mammals, e.g., dogs, cats, rabbits, cattle, horses, sheep, goats, swine, and deer, and non-mammals, e.g., birds and the like.

"Disease" specifically includes any unhealthy condition of an animal or part thereof and includes an unhealthy condition which may be caused by, or incident to, medical or veterinary therapy applied to that animal, i.e., the "side effects" of such therapy.

"Pharmaceutically acceptable" means that which is useful in preparing a pharmaceutical composition that is generally safe, non-toxic and neither biologically nor otherwise undesirable and includes that which is acceptable for veterinary use as well as human pharmaceutical use.

"Pharmaceutically acceptable salts" means salts which are pharmaceutically acceptable, as defined above, and which possess the desired pharmacological activity. The compounds of Formula 1, 2, 3 and 4 have a basic nitrogen which is capable of reacting with organic or inorganic acids to form an acid addition salt. Acceptable inorganic acids include hydrochloric acid, hydrobromic acid, sulfuric acid, nitric acid, phosphoric acid, and the like. Acceptable organic acids include acetic acid, propionic acid, hexanoic acid, heptanoic acid, cyclopentanepropionic acid, glycolic acid, pyruvic acid, lactic acid, malonic acid, succinic acid, malic acid, maleic acid, fumaric acid, tartaric acid, citric acid, benzoic acid, o-(4-hydroxybenzoyl)benzoic acid, cinnamic acid, mandelic acid, methanesulfonic acid, ethanesulfonic acid, 1,2,-ethanedisulfonic acid, 2-hydroxyethanesulfonic acid, benzenesulfonic acid p-chlorobenzenesulfonic acid, 2-naphthalenesulfonic acid, p-toluenesulfonic acid, camphorsulfonic acid, 4-methylbicyclo[2.2.2]oct-2-ene-1-carboxylic acid, glucoheptonic acid, 4,4'-methylenebis(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like.

"N-Oxide derivative" means a compound of Formula I in which the nitrogen atom in the 1'-azabicyclo[2.2.2]oct-3'S-yl moiety is in an oxidized state. N-oxide derivatives can be readily prepared by methods known to those of ordinary skill in the art. For example, the N-oxide derivatives of the compounds of Formula I can be prepared by treating an unoxidized form of the compound of Formula I with an oxidizing agent (e.g., trifluoroperacetic acid, permaleic acid, perbenzoic acid, peracetic acid, meta-chloroperoxybenzoic acid, etc.) in a suitable solvent (e.g., a halogenated hydrocarbon such as methylene chloride) at approximately 0° C. Compounds of Formula I in unoxidized form can be prepared from N-oxides of compounds of Formula I by treating with a reducing agent (e.g., sulfur, sulfur dioxide, triphenyl phosphines, lithium borohydride, sodium borohydride, phosphorus trichloride, tribromide, etc.) in an suitable solvent (e.g., acetonitrile, ethanol, aqueous dioxane, etc.) at 0° to 80° C.

"O-β-D-Glucuronide conjugate" means a compound of Formula I in which the hydroxy group at the 6-position forms a conjugate with glucuronic acid. Such conjugates are in vivo hydrolyzable and can act as prodrugs. O-β-D-Glucuronide conjugates can be readily prepared by methods known to those of ordinary skill in the art. For example, the O-β-D-glucuronide conjugates of the compounds of Formula I can be prepared by reacting an unconjugated form of the compound of Formula I with methyl (2,3,4-tri-O-acetyl-α-D-glucopyranosyl bromide)uronate and then deprotecting by alkaline hydroysis (see Bollenback, G. N., Long, J. W., Benjamin, D. G., Lindquist, J. A.; *Am. Chem. Soc.* 1955, 77, 3310–3315). Alternatively, the O-β-D-glucuronide conjugates of the compounds of Formula I can be prepared by enzyme synthesis using an immobilized preparation of solubilized hepatic microsomal glutathione transferass (see Pallante, S. L., Lisek, C. A., Dulik, D. M., Fenselau, C. F.; *Drug Metabolism and Disposition* 1986; 14(3):313–318).

"Optional" or "optionally" means that the subsequently described event or circumstance may or may not occur, and that the description includes instances where the event or circumstance occurs and instances in which it does not. For example, "optionally converting 2-(1'-azabicyclo[2.2.2]oct-3'S-yl)-6-hydroxy-2,3,3a,4,5,6-hexahydro-1H-benz[de] isoquinolin-1-one in to a pharmaceutically acceptable acid addition salt" means that the conversion to the acid addition salt may or may not be carried out in order for the process described to fall within the invention, and the invention includes those processes wherein the conversion occurs and those processes in which it does not.

"Therapeutically effective amount" means that amount which, when administered to an animal for treating a disease, is sufficient to effect such treatment for the disease.

"Treating" or "treatment" of a disease includes: (1) preventing the disease from occurring in an animal which may be predisposed to the disease but does not yet experience or display symptoms of the disease, (2) inhibiting the disease, i.e., arresting its development, or (3) relieving the disease, i.e., causing regression of the disease.

Isomerism is the phenomenon wherein compounds have identical molecular formulae but differ in the nature or sequence of bonding of their atoms or in the arrangement of their atoms in space. Isomers that differ in the arrangement of their atoms in space are termed "stereoisomers". Stereoisomers that are not mirror images of one another are termed "diastereomers" and stereoisomers that are nonsuperimposable mirror images are termed "enantiomers" or sometimes optical isomers. A carbon atom bonded to four nonidentical substituents is termed a "chiral center".

A compound with one chiral center has two enantiomeric forms of opposite chirality and may exist as either an individual enantiomer or as a mixture of enantiomers. A mixture containing equal amounts of individual enantiomeric forms of opposite chirality is termed a "racemic mixture". A compound that has more than one chiral center has $2^{n-1}$ enantiomeric pairs, where n is the number of chiral centers. Compounds with more than one chiral center may exist as either an individual diastereomer or as a mixture of diastereomers, termed a "diastereomeric mixture". For the purposes of this application, a mixture of stereoisomers containing one or more enantiomeric pairs is termed "enantiomeric" and a mixture of stereoisomers without their respective enantiomers present is termed "non-enantiomeric".

When one chiral center is present a stereoisomer may be characterized by the absolute configuration of that chiral center. Absolute configuration refers to the arrangement in space of the substituents attached to the chiral center. The substituents attached to the chiral center under consideration are ranked in accordance with the *Sequence Rule* of Cahn, Ingold and Prelog and the absolute descriptor R or S is cited in parentheses followed by a hyphen and the chemical name of compound (e.g., (S)-2-(1'-azabicyclo[2.2.2]oct-3-ylamine).

For the purposes of this application, when two or more chiral centers are present, the descriptor is cited immediately following the number of the chiral center as it appears in the name of the compound. When a chiral center can be of either configuration individually or as a mixture thereof, in equal amounts or otherwise, or when a chiral center can exist only as a mixture of the two configurations, in equal amounts or otherwise, no descriptor will appear. Accordingly, the compound of Formula I in which the optional bond is not present and each chiral center is in an S-configuration, that is, the compound of the following formula:

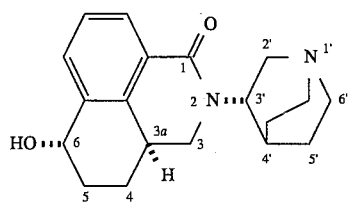

is referred to as 2-(1'-azabicyclo[2.2.2]oct-3'S-yl)-6S-hydroxy-2,3,3aS,4,5,6-hexahydro-1H-benz[de] isoquinolin-1-one.

Preferred Embodiments

While the breadth of compounds which are intended by the invention is as set forth in the Summary of the Invention, certain compounds are preferred. For example, preferred compounds are the compounds of Formula I wherein the optional bond is not present and more preferably wherein the compound is the (3aS,3'S)-diastereomers thereof, particularly the (6R,3aS,3'S)-diastereomer thereof, namely 2-(1'-azabicyclo[2.2.2]oct-3'S-yl)-6R-hydroxy-2,3,3aS,4,5,6-hexahydro-1H-benz[de] isoquinolin-1-one.

Pharmacology and Utility

The 5-HT$_3$ receptor binding affinity of the compounds of this invention can be readily determined by an accepted in vitro assay which measures the affinity of the test compound for 5-HT$_3$ receptors in membranes prepared from NB 108-15 cells. The 5-HT$_3$ receptor affinity binding assay, as adapted for testing the compounds of Formula I, is described in Example 9.

In addition, the 5-HT$_3$ receptor antagonist activity of the compounds of this invention can be determined by an art-recognized/n vivo assay which measures the inhibition by a test compound of the von Bezold-Jarisch reflex in anesthetized rats (e.g., see Butler, A., Hill, J. M., Ireland, S. H., Hordon, C. C., Tylers, M. B.; *Brit. J. Pharmacol.* 1988; 94:397–412; Cohen, M. L., Bloomquist, W., Gidda, J. S., Lacefield, W.; *J. Pharmacol. Exp. Ther.* 1989; 248:197–201; Fozard, J. R.; MDL 72222: *Arch. Pharmacol.* 1984; 326:36–44). The 5-HT$_3$ receptor antagonists assay, as adapted for testing the compounds of Formula I, is described in Example 10.

As 5-HT$_3$ receptor antagonists the compounds of Formula I can be used for treating a broad range of diseases in animals, particularly humans. For example, the compounds of Formula I can be used in treating emesis, gastrointestinal disorders, central nervous system (CNS) disorders, cardiovascular disorders or pain.

Emesis treatable with the compounds of Formula I include emesis caused by surgical anesthesia, psychological stress, pregnancy, certain disease states, radiotherapy, radiation poisoning and toxic substances. Disease states which are known to induce emesis include conditions such as gut obstruction, raised intracranial pressure, acute myocardial infarction, migraine headaches and adrenal crisis. Toxic substances which induce emesis include toxins in the form of abnormal metabolites or abnormal accumulation of naturally occurring substances associated with such conditions as hepatic coma, renal failure, diabetic ketoacidosis, hyperthyroid crisis, both hypo- and hyperparathyroidism and Addison's disease or ingested toxins such as enterotoxins in staphylococcus-contaminated food or drugs administered for therapeutic purposes such as digitalis, emetine or chemotherapeutic agents.

The compounds of Formula I are of particular value in treating (especially preventing) the emesis induced by radiation poisoning, treatment for cancer with radiotherapy or chemotherapy with cytotoxic agents or drug therapy in general wherein a significant side effect is emesis (e.g., amphotericin B in treating immunosuppressed patients, zidovudine (AZT) in the treatment of AIDS and interleukin in treating cancer).

Gastrointestinal diseases treatable with the compounds of Formula include diseases of the stomach, esophagus and of both the large and small intestines. Examples of specific diseases include, but are not limited to, dyspepsia (e.g., non-ulcer dyspepsia), gastric stasis, peptic ulcer, reflux esophagitis, flatulence, bile reflux syndrome (which may result in chronic constipation and diarrhea), diverticular disease, biliary dysmotility (which may result in sphincter of Oddi dysfunction and "sludge" or microscopic crystals in the gall bladder), gastroparesis (e.g., diabetic, postsurgical or idiopathic), irritable bowel syndrome and retarded gastric emptying. The compounds of Formula I are also useful as short-term prokinetics to facilitate diagnostic radiology and intestinal intubation. In addition, the compounds are useful for treating diarrhea, particularly diarrhea induced by cholera and carcinoid syndrome.

Diseases of the central nervous system treatable with the compounds of Formula I include cognitive disorder, psychoses, obsessive/compulsive and anxiety/depression behavior. Cognitive disorders include attentional or memory deficit, dementia stated (including senile dementia or the Alzheimer's type and aging), cerebral vascular deficiency and Parkinson's disease. Psychoses that are treatable using the compounds of Formula I include paranoia, schizophrenic and autism. Representative, treatable anxiety/depressive states include anticipatory anxiety (e.g., prior to surgery, dental work, etc.) depression, mania, convulsions and anxiety caused by withdrawal from addictlye substances such as opiates, benzodiazapines, nicotine, alcohol, cocaine and other drugs of abuse.

Cardiovascular diseases treatable with the compounds of Formula I include arrhythmias and hypertension. Pain treatable with the compounds of Formula I include the pain associated with cluster headaches, migraines, trigeminal neuralgia and visceral pain such as that caused by abnormal distension of hollow visceral organs.

The anti-emetic activity of the compounds of this invention can be determined by art-recognized assay which measures the reduction produced by the test compound of cisplatin-induced emesis in ferrets (e.g., Costall, B., Domehey, A. M., Naylor, R. J., and Tattersall, F. D.; *Neuropharmacology* 1986; 25(8): 959–961; Miner, W. D. and Sanger, G. J.; *Brit. J. Pharmacol.* 1986; 88: 497–499). The ferret, anti-emetic assay, as adapted for testing the compounds of Formula I, described in Example 11.

Anti-emetic activity of the compounds of this invention can be determined by art-recognized assay which measures the reduction produced by the test compound of cisplatin-induced emesis in dogs (e.g., Smith, W. L., Alphin, R. S., Jackson, C. B., and Sancilio, L. F.; *J. Pharm. Pharmacol.* 1989; 41:101–105; Gylys, J. A.; *Res. Commun. Chem. Pathol. Pharmacol.* 1979; 23(1): 61–68). The dog, anti-emetic assay, as adapted for testing the compounds of Formula I, is described in Example 12.

The prokinetic activity of compounds of this invention can be determined by measuring the increase in rate of gastric emptying in rats after oral administration of test compound. The rat, prokinetic assay is a well established model for identifying compounds that possess prokinetic activity (e.g., see Droppleman, D., Gregory, R., Alphin, R. S.; *J. Pharmacol. Methods* 1980; 4(3): 227–30) and is described in Example 13.

The cognitive enhancing properties of compounds of this invention can be determined by using the Morris Water Maze Assay, which measures changes in the cognitive performance of rats. The Morris Water Maze Assay is a well established model for demonstrating cognition enhancing activity (e.g., see Morris, R. G. M., Garrud, P., Rawline, J. N. P., O'Keefe, J.; *Nature.* 1982; 297: 681–683) and is described in Example 16.

Anxiolytic activity is determined by the art-recognized Crawley and Goodwin two-compartment exploratory model (e.g., see Kilfoil, T., Michel, A., Montgomery, D., Whiting, R. L.; *Neuropharmacology* 1989; 28(9): 901–905). In brief, the method measures the extent a compound affects the natural anxiety of mice in a novel, brightly lighted area. The anxiolytic behavior assay is described in Example 14.

Anxiolytic activity during withdrawal from drugs of abuse is determined by the mouse, withdrawal anxiety test, an accepted assay (e.g., see Carboni, E., Acquas, E., Leone, P., Perezzani, L., Di Chiara, G.; *Eur. J. Pharmacol* 1988; 151:159–160). This procedure utilizes the exploratory model described above to measure the extent a compound ameliorates the symptoms of withdrawal that occur after chronically treating with an addictlye substance and then abruptly ceasing the treatments. The withdrawal anxiety assay is described in Example 15.

In summary, the compounds of this invention are useful for treating conditions which can be ameliorated by antagonism of 5-HT$_3$ receptors. Such conditions include emesis, CNS disorders, gastrointestinal disorders, cardiovascular disorders and pain.

Administration and Pharmaceutical Composition

In general, compounds of the invention will be administered in therapeutically effective amounts via any of the usual and acceptable modes known in the art, either singly or in combination with another compound of Formula I or with another therapeutic agent. A therapeutically effective amount may vary widely depending on the severity of the disease, the age and relative health of the subject, the potency of the compound used and other factors. A therapeutically effective amount may range from approximately 0.01 milligram per Kg (mg/Kg) body weight per day to 10 mg/Kg body weight per day. Preferably the amount will be approximately 0.1 to 1 mg/Kg/day. Therefore, a therapeutically effective amount for a 70 Kg human may range from 0.7 to 700 mg/day, preferably 7 to 70 mg/day.

One of ordinary skill in the art of treating such diseases will be able, without undue experimentation and in reliance upon personal knowledge and the disclosure of this application, to ascertain a therapeutically effective amount of a compound of Formula I for a given disease.

In general, compounds of the invention will be administered as pharmaceutical compositions by one of the following routes: oral, systemic (e.g., transdermal, intranasal or by suppository) or parenteral (e.g., intramuscular, intravenous or subcutaneous). Compositions can take the form of tablets, pills, capsules, semisolids, powders, sustained release formulations, solutions, suspensions, elixirs, aerosols, or any other appropriate composition and are comprised of, in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk, and the like. Liquid and semisolid excipients may be selected from water, ethanol, glycerol, propylene glycol and various oils, including those of petroleum, animal, vegetable or synthetic origin (e.g., peanut oil, soybean oil, mineral oil, sesame oil, etc.). Preferred liquid carriers, particularly for injectable solutions, include water, saline, aqueous dextrose and glycols.

Compressed gases may be used to disperse the compound of the invention in aerosol form. Inert gases suitable for this purpose are nitrogen, carbon dioxide, nitrous oxide, etc. Other suitable pharmaceutical carriers and their formulations are described in A. R. Alfonso; *Remington's Pharmaceutical Sciences* 1985; 17th ed. Easton, Pa.: Mack Publishing Company.

The amount of a compound of the invention in the composition may vary widely depending upon the type of formulation, size of a unit dosage, kind of excipients and other factors known to those of skill in the art of pharmaceutical sciences. In general, the final composition will comprise from 25% w to 75% w of the compound of Formula I, preferably 30% w to 50% w, with the remainder being the excipient or excipients.

Preferably the pharmaceutical composition is administered in a single unit dosage form for continuous treatment or in a single unit dosage form ad libitum when relief of symptoms is specifically required. Representative pharmaceutical formulations containing a compound of Formula I are described in Example 8.

Processes of the Invention

The processes of this invention are depicted in the following reaction scheme:

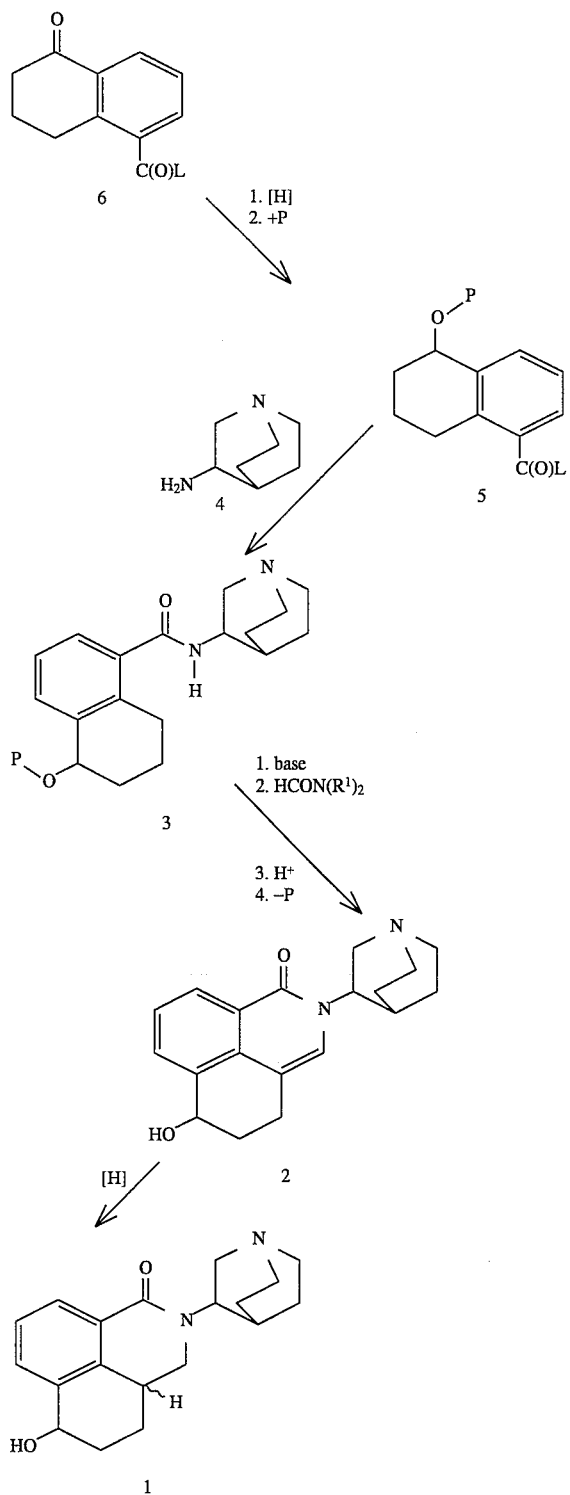

in which L is a leaving group and $R^1$ is $(C_{1-4})$alkyl.

A diastereomeric mixture of 2-(1'-azabicyclo[2.2.2]oct-3'-yl)-6-hydroxy-2,3,3a,4,5,6-hexahydro-1H-benz[de] isoquinolin-1-one (Formula 1) is prepared by hydrogenating 2-(1'-azabicyclo[2.2.2]oct-3'-yl)-6-hydroxy-2,4,5,6-tetrahydro-1H-benz[de] isoquinolin-1-one (Formula 2). The hydrogenation can be carried out by any means which hydrogenates at the 3- and 3a-positions without dehydroxylating at the 6-position. Such a means can comprise hydrogenating in the presence of a suitable catalyst (e.g., 10% palladium on carbon (10% Pd/C), 5% palladium on barium sulfate (5% Pd/BaSO₄), 5% palladium on alumina (5% Pd/Al₂O₃), 10% palladium on strontium carbonate (10% Pd/SrCO₃), etc., preferably 5% Pd/BaSO₄) and in a suitable organic solvent, typically an ether, alcohol, carboxylic acid, ester, amide or aromatic hydrocarbon and preferably an alcohol (e.g., tetrahydrofuran (THF), ethanol, acetic acid, ethyl acetate, N,N-dimethylformamide (DMF), toluene, etc., preferably ethanol.), at 10° to 78° C., typically at 15° to 30° C. and preferably at approximately 20° C., and at 0 to 200 psig, typically 0 to 100 psig and preferably at approximately atmospheric pressure, and requires 24 to 80 hours. The preparation of a compound of Formula i is described in Example 7.

The compound of Formula 2 is prepared by reacting protected N-(1'-azabicyclo[2.2.2]oct-3'S-yl)-5-hydroxy-5,6,7,8-tetrahydro-1-naphthalenecarboxamide (Formula 3) with 1 to 20 molar equivalents, typically 1 to 10 molar equivalents and preferably approximately 3 molar equivalents, of a dialkylformamide, typically a di$(C_{1-4})$alkylformamide and preferably DMF, acidifying and then deprotecting. The reaction with the formamide is carried out in the presence of a strong base, typically sodium hydride or an alkyllithium base and preferably butyllithium (e.g., sec-butyllithium, n-butyllithium, etc., preferably sec-butyllithium), and in a suitable solvent, typically an ether (e.g., diethyl ether, dimethoxyethane, tetrahydrofuran (THF), etc., preferably THF), under an inert atmosphere (e.g., nitrogen or argon) at −20° to −75° C., typically at −65° to −75° C. and preferably at approximately −74° C., and requires 0.5 to 5 hours. The reaction mixture is then warmed to between 0° and 30° C., typically to between 15° and 25° C. and preferably to approximately 20° C., and excess molar equivalents of acid, typically 5 to 15 molar equivalents of acid and preferably approximately 10 molar equivalents of hydrochloric acid, is added and the acidified mixture is stirred for 2 to 5 hours.

The deprotection can be carried out by any means which removes the protective group to give the desired unprotected product in reasonable yield. For example, a convenient deprotecting method, particularly when the protective group is tert-butyldiphenylsilyl comprises reacting the protected compound with tetrabutylammonium fluoride in a suitable solvent, typically an ether and preferably THF. The deprotection is carried out in suitable organic solvent at 0° to 50° C., typically at 15° to 25° C. and preferably at approximately 20° C., and requires 1 to 24 hours. A detailed description of the techniques applicable to protective groups and their removal can be found in Greene, T. W.; *Protective Groups in Organic Synthesis* 1981; John Wiley & Sons, Inc.. The preparation of a compound of Formula 2 is described in Example 5.

The compound of Formula 3 is prepared by reacting a protected 5-hydroxy-1,2,3,4-tetrahydro-1-naphthoic acid derivative (Formula 5) with 1-azabicyclo[2.2.2]oct-3-ylamine (Formula 4). The reaction is carried out under a nitrogen atmosphere in a suitable inert organic solvent, typically an aromatic hydrocarbon, halogenated hydrocarbon or ether and preferably an aromatic hydrocarbon (e.g., toluene, methylene chloride, THF, etc. preferably toluene), at 20° to 200° C., typically at 90° to 130° C. and preferably at approximately 120° C., and requires 10 to 72 hours. The preparation of a compound of Formula 3 is described in Example 4.

The 1-azabicyclo[2.2.2]oct-3-ylamine is commercially available or can be readily prepared by methods known to those of ordinary skill in the art. The compound of Formula 5 is prepared by reducing a 5-oxo-1,2,3,4-tetrahydro-1- naphthoic acid derivative (Formula 6) to give a corresponding unprotected 5-hydroxy-1,2,3,4-tetrahydro-1-naphthoic acid derivative and then protecting. The reduction can be effected with a suitable reducing agent, preferably an alkali borohydride (e.g., sodium borohydride, lithium borohydride, etc. preferably sodium borohydride) in a suitable solvent, typically an alcohol (e.g., methanol, ethanol, propanol, isopropanol, etc., preferably ethanol), at −20° to 30° C., typically at −10° to 30° C. and preferably at approximately 0° C., and requires 1 to 5 hours. A suitable protective group can be created by reacting the 5-hydroxy-1,2,3,4-tetrahydro-1-naphthoic acid derivative with 1 to 5 molar equivalents of a suitable protective agent (e.g., tert-butyldiphenylsilyl chloride, tert-butyldimethylsilyl chloride, etc., preferably tert-butyldiphenylsilyl chloride) in a suitable solvent (e.g., DMF, methylene chloride, etc., preferably DMF). For example, a compound of Formula 5 wherein P is tert-butyldiphenylsilyl is prepared by reacting the unprotected 5-hydroxy-1,2,3,4-tetrahydro-1-naphthoic acid derivative with tert-butyldiphenylsilyl chloride in the presence of imidazole in DMF. The reaction is carried out at 0° to 60° C., typically 0° to 40° C. and preferably at approximately 20° C., and requires 1 to 30 hours. The preparation of a compound of Formula 5 is described in Example 3.

Compounds of Formula 6 in which L is hydroxy or $(C_{1-4})$alkoxy can be prepared by reacting 2-methyl-5,6,7,8-tetrahydro-2H-1-benzopyran-5-one with propiolic acid or $(C_{1-4})$alkyl propiolate, respectively. Preferably the reaction is carried out with ethyl propiolate at 20° to 150° C., typically at 50° to 140° C. and preferably at approximately 115° C. and requires 1 to 5 hours. Other leaving groups can be prepared by treating a compound of Formula 6 in which L is hydroxy with an appropriate agent (e.g., methanesulfonyl chloride, thionylchloride, phosphorous pentachloride, phosphorous oxychloride, etc.). For example, a compound of Formula 6 in which L is chloro can be prepared by reacting 5-oxo-5,6,7,8-tetrahydro-1-naphthoic acid with thionyl chloride in a suitable solvent, typically an aromatic hydrocarbon or halogenated hydrocarbon (e.g., toluene, methylene chloride, etc. preferably toluene), at 25° to 50° C., typically at 40° to 50° C. and preferably at approximately 50° C., and requires 1 to 2 hours. The preparation of a compound of Formula 6 is described in Example 2.

The 2-methyl-5,6,7,8-tetrahydro-2H-1-benzopyran-5-one is prepared by reacting 1,3-cyclohexanedione with crotonaldehyde. The reaction is carried out in a suitable solvent (e.g., pyridine, methylpyridine, 2,4-lutidine, pyrrolidine, etc., preferably pyridine) under an inert atmosphere (e.g., argon or nitrogen) at 100° to 130° C., typically at 110° to 120° C. and preferably at approximately 115° C., and requires 1 to 24 hours. The preparation of 2-methyl-5,6,7,8-tetrahydro-2H-1-benzopyran-5-one is described in Example 1.

Depending upon the reaction conditions, isolation/separation techniques and starting materials, the compounds of Formulae 1, 2, 3 and 4 may be converted to or prepared as their non-salt or salt forms. Thus, the compounds of Formula 1, 2, 3 and 4 may be utilized in the processes of this invention as a non-salt or salt form in order for the process described to fall within the invention, and the invention includes those processes wherein the compounds are in non-salt form and those processes wherein the compounds are salts. Accordingly, while some forms of the compounds of Formulae 1, 2, 3 and 4 are preferred, unless indicated otherwise, the description or naming of a particular compound in the specification or in the claims is intended to include both the non-salt form and salt forms, pharmaceutically acceptable or otherwise, thereof.

The compounds of Formulae 1, 2, 3, 4 and 5 each contain one or more chiral centers and can be separated into or prepared as individual stereoisomers and/or mixtures of stereoisomers. Accordingly, while some stereoisomers or mixtures of stereoisomers of the compounds of Formulae 1, 2, 3, 4 and 5 are preferred, unless indicated otherwise, the description or naming of a particular chiral compound in the specification or in the claims is intended to include individual stereoisomers and the mixtures, racemic or otherwise, thereof.

The individual stereoisomers of the compound of Formula 1 can be separated from a non-enantiomeric diastereomeric mixture of the compound of Formula 1 by chromatography, by separation/resolution techniques based upon differences in solubility, by direct or selective crystallization or by any other method known to one of ordinary skill in the art. For example, 2-(1'-azabicyclo[2.2.2]oct-3'S-yl)-6R-hydroxy-2,3,3aS,4,5,6-hexahydro-1H-benz[de] isoquinoline-1-one is readily prepared from a diastereomeric mixture of 2-(1'-azabicyclo[2.2.2]oct-3'S-yl)-6R-hydroxy-2,3,3a,4,5,6-hexahydro-1H-benz[de]isoquinolin-1-one by silica gel column chromatography and is described in Example 6.

A non-enantiomeric diastereomeric mixture of the compound of Formula 1 can be prepared by reacting an enantiomeric diastereomeric mixture with an optically active acid (e.g., tartaric acid, mandelic acid, malic acid, the 2-arylpropionic acids in general, camphorsulfonic acid, etc.) to form diastereomeric crystalline salts. The non-enantiomeric mixture of crystalline salts is then separated into individual diastereomers by any of the methods described above and the pure diastereomers of the compound of Formula 1 are recovered, along with the optically active acid, by any practical means that would not result in racemization. A more detailed description of the techniques applicable to the preparation of stereoisomers can be found in Jean Jacques, Andre Collet, Samuel H. Wilen, Enantiomers, Racemates and Resolutions, John Wiley & Sons, Inc. (1981).

A non-enantiomeric diastereomeric mixture of the compound of Formula 1 containing the (6R,3aR,3'S)-, (6S,3aS, 3'S)-, (6R,3aS,3'S)- and (6S,3aR,3'S)-diastereomers can be prepared by proceeding as described above and hydrogenating a diastereomeric mixture of 2-(1'-azabicyclo[2.2.2]oct-3'S-yl)-6-hydroxy-2,4,5,6-tetrahydro-1H-benz[de] isoquinolin-1-one. A diastereomeric mixture of the compound of Formula 1 containing a mixture of the (6S,3aR,3'S)- and (6S,3aS,3'S)-diastereomers or a mixture of the (6R,3aR,3'S)- and (6R,3aS,3'S)-diastereomers can be prepared by proceeding as described above and hydrogenating 2-(1'-azabicyclo [2.2.2]oct-3'S-yl)-6S-hydroxy-2,4,5,6-tetrahydro-1H-benz [de] isoquinolin-1-one or 2-(1'-azabicyclo[2.2.2]oct-3'S-yl)-6R-hydroxy-2,4,5,6-tetrahydro-1H-benz[de] isoquinolin-1-one, respectively. The individual diastereomers of the compound of Formula 1 can then be separated by any of the separation/resolution techniques described above.

The 2-(1'-azabicyclo[2.2.2]oct-3'S-yl)-6-hydroxy-2,4,5, 6-tetrahydro-1H-benz[de] isoquinolin-1-one can be prepared as a diastereomeric mixture by proceeding as described above and reacting a diastereomeric mixture of protected N-(1'-azabicyclo[2.2.2]oct-3'S-yl)-5-hydroxy-5,6, 7,8-tetrahydro-1-naphthalenecarboxamide with a dialkylformamide in the presence of base, acidifying and then deprotecting. The individual diastereomers of 2-(1'-azabicyclo [2.2.2]oct-3'S-yl)-6-hydroxy-2,4,5,6-tetrahydro-1H-benz [de] isoquinolin-1-one can be prepared from a diastereomeric mixture by any of the applicable separation/resolution techniques described above or by proceeding as described above or from the corresponding individual diastereomer of the protected N-(1'-azabicyclo[2.2.2]oct-3'S-yl)-5-hydroxy-5,6,7,8-tetrahydro-1-naphthalenecarboxamide.

A diastereomeric mixture of protected N-(1'-azabicyclo[2.2.2]oct-3'S-yl)-5-hydroxy-5,6,7,8-tetrahydro-1-naphthalenecarboxamide can be prepared by proceeding as described above and reacting an enantiomeric mixture of the compound of Formula 5 with (S)-1-azabicyclo[2.2.2]oct-3-ylamine. The individual diastereomers of protected N-(1'-azabicyclo[2.2.2]oct-3'S-yl)-5-hydroxy-5,6,7,8-tetrahydro-1-naphthalenecarboxamide can be prepared from a mixture of the diastereomers by any of the separation/resolution techniques described above or can be prepared by proceeding as described above and reacting an individual enantiomer of the compound of Formula 5 with (S)-1-azabicyclo[2.2.2]oct-3-ylamine.

The individual enantiomers of the compounds of Formula 5 can be prepared from the individual enantiomers of the corresponding unprotected 5-hydroxy-1,2,3,4-tetrahydro-1-naphthoic acid derivative. The individual enantiomers of the unprotected 5-hydroxy-1,2,3,4-tetrahydro-1-naphthoic acid derivative can be prepared by reacting an enantiomeric mixture with an optically active base to form diastereomeric crystalline salts, separating the diastereomeric salts by chromatography, by separation/resolution techniques based upon differences in solubility, by direct or selective crystallization or by any other method known to one of ordinary skill in the art, and then recovering the pure enantiomers, along with the optically active base, by any practical means that would not result in racemization (e.g., see *Enantiomers, Racemates and Resolutions* 1981; John Wiley & Sons, Inc. cited above).

Alternatively, the individual enantiomers of the unprotected 5-hydroxy-1,2,3,4-tetrahydro-1-naphthoic acid derivative can be prepare by an enantioselective reduction of the compound of Formula 6. The enantioselective reduction is carried out by proceeding as described above and reducing the compound of Formula 6 in the presence of a suitable chiral auxiliary (e.g., azaoxaborodine) or a selective reducing agent (e.g, chlorodiisopinocampheylborane, lithium tri-sec-butylborohydride, etc.). For example, an unprotected 5-hydroxy-1,2,3,4-tetrahydro-1-naphthoic acid derivative wherein the chiral carbon is in the (R)-configuration can be prepared by proceeding as described above and reducing the compound of Formula 6 with diborane in the presence of (S)-1-aza-2-boro-3-oxa-4,4-diphenyl[3.3.0]bicyclooctane. Similarly, an unprotected 5-hydroxy-1,2,3,4-tetrahydro-1-naphthoic acid derivative wherein the chiral carbon is in the (S)-configuration can be prepared by proceeding as described above and reducing the compound of Formula 6 in the presence of (R)-1-aza-2-boro-3-oxa-4,4-diphenyl[3.3.0]bicyclooctane. For a more detailed description of the techniques applicable to the enantioselective reduction of unsymmetrical ketones see Singh, V. K.; *Synthesis* 1992; 7:605.

(S)-1-Azabicyclo[2.2.2]oct-3-ylamine can be prepared by separating the individual enantiomers from a enantiomeric mixture of the amine by any of the applicable separation/resolution techniques described above. Alternatively, (S)-1-azabicyclo[2.2.2]oct-3-ylamine can be prepared by reacting 1-azabicyclo[2.2.2]oct-3-one with an (R)-α-alkylbenzylamine, preferably (R)-1-phenylethylamine, to give the corresponding (R)-N-(α-alkylbenzyl)-3-(1-azabicyclo[2.2.2]octan)imine, reducing the imine to give the corresponding N-(1R-phenylalkyl)-1-azabicyclo[2.2.2]oct-3S-ylamine and then hydrogenolyzing. The reaction with the (R)-α-alkylbenzylamine is carried out in the presence of lithium oxide in a suitable organic solvent, typically an ether and preferably THF, at 10° to 40° C., typically at 15° to 30° C. and preferably at approximately 20° C., and requires 12 to 84 hours. The reduction of the imine can be carried out by catalytic hydrogenation or with a suitable chemical reducing agent.

Hydrogenation of the imine is carried out in the presence of a suitable catalyst preferably 5% Pt/C, and in a suitable organic solvent, typically an alcohol and preferably ethanol, at 10° to 40° C., typically at 15° to 30° C. and preferably at approximately 20° C., and at 0 to 100 psig, typically at 0 to 50 psig and preferably at approximately 20 psig, and requires 1 to 48 hours. Alternatively, the imine can be reduced with a suitable chemical reducing agent, preferably an alkali borohydride (e.g., sodium borohydride, lithium borohydride, etc., preferably sodium borohydride), in a suitable organic solvent, typically an alcohol and preferably ethanol, at –15° to 50° C., typically at 15° to 30° C. and preferably at approximately 20° C., and requires 15 minutes to 3 hours.

The hydrogenolyzation is effected by hydrogenation the N-(1R-phenylalkyl)-1-azabicyclo[2.2.2]oct-3S-ylamine in the presence of a suitable catalyst (e.g., 10% Pd/C, 20% Pd/C, etc., preferably 10% Pd/C) and in a suitable organic solvent, typically an alcohol and water mixture and preferably 5/1 to 2/1 ethanol/water, at 10° to 40° C., typically at 15° to 30° C. and preferably at approximately 20° C., and at 0 to 100 psig, typically at 0 to 20 psig and preferably at approximately 5 psig, and requires 5 to 48 hours.

Thus, the compounds of Formulae 1, 2, 3, 4 and 5 may exist as individual stereoisomers and/or any mixture of stereoisomers in order for the process described to fall within the invention, and the invention includes those processes wherein individual stereoisomers are used and those processes wherein mixtures of stereoisomers are used. An exemplary method of practicing the process of this invention comprises:

(A) reacting an enantiomeric mixture of a compound of Formula 5 with (S)-1-azabicyclo[2.2.2]oct-3-ylamine to give a diastereomeric mixture of a compound of Formula 3(a):

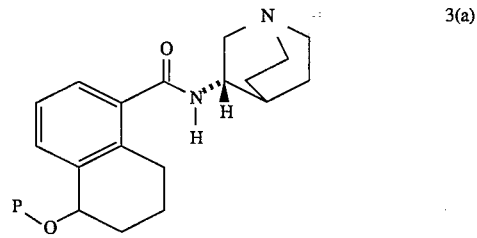

3(a)

in which P is a protective group;

(B) reacting the diastereomeric mixture of the compound of Formula 3(a) with a dialkylformamide in the presence of a strong base, acidifying and then deprotecting to give a diastereomeric mixture of 2-(1'-azabicyclo[2.2.2]oct-3'S-yl)-6-hydroxy-2,4,5,6-tetrahydro-1H-benz[de] isoquinolin-1-one;

(C) separating the diastereomeric mixture of 2-(1'-azabicyclo[2.2.2]oct-3'S-yl)-6-hydroxy-2,4,5,6-tetrahydro-1H-benz[de] isoquinolin-1-one into individual diastereomers to give 2-(1'-azabicyclo[2.2.2]oct-3'S-yl)-6R-hydroxy-2,4,5,6-tetrahydro-1H-benz[de] isoquinolin-1-one and 2-(1'-azabicyclo[2.2.2]oct-3'S-yl)-6S-hydroxy-2,4,5,6-tetrahydro-1H-benz[de] isoquinolin-1-one;

(D) hydrogenating the 2-(1'-azabicyclo[2.2.2]oct-3'S-yl)-6R-hydroxy-2,4,5,6-tetrahydro-1H-benz[de] isoquinolin-1-one or the 2-(1'-azabicyclo[2.2.2]oct-3'R-yl)-6S-hydroxy-2,4,5,6-tetrahydro-1H-benz[de] isoquinolin-1-one to give a diastereomeric mixture of 2-(1'-azabicyclo[2.2.2]oct-3'S-yl)-6R-hydroxy-2,3,3a,4,5,6-hexahydro-1H-benz[de] isoquinolin-1-one or 2-(1'-azabicyclo[2.2.2]oct-3'S-yl)-6S-hydroxy-2,3,3a,4,5,6-hexahydro-1H-benz[de] isoquinolin-1-one, respectively;

(E) separating the diastereomeric mixture of 2-(1'-azabicyclo[2.2.2]oct-3'S-yl)-6R-hydroxy-2,3,3a,4,5,6-hexahydro-1H-benz[de] isoquinolin-1-one into individual diastereomers to give 2-(1'-azabicyclo[2.2.2]oct-3'S-yl)-6R-hydroxy-2,3,3aR,4,5,6-hexahydro-1H-benz[de] isoquinolin-1-one and 2-(1'-azabicyclo[2.2.2]oct-3'S-yl)-6R-hydroxy-2,3,3aS,4,5,6-hexahydro-1H-benz[de] isoquinolin-1-one;

(F) separating the diastereomeric mixture of 2-(1'-azabicyclo[2.2.2]oct-3'S-yl)-6S-hydroxy-2,3,3a,4,5,6-hexahydro-1H-benz[de] isoquinolin-1-one into individual diastereomers to give 2-(1'-azabicyclo[2.2.2]oct-3'S-yl)-6S-hydroxy-2,3,3aR,4,5,6-hexahydro-1H-benz[de] isoquinolin-1-one and 2-(1'-azabicyclo[2.2.2]oct-3'S-yl)-6S-hydroxy-2,3,3aS,4,5,6-hexahydro-1H-benz[de] isoquinolin-1-one; and (G) converting an individual diastereomer of 2-(1'-azabicyclo[2.2.2]oct-3'S-yl)-6-hydroxy-2,3,3a,4,5,6-hexahydro-1H-benz[de] isoquinolin-1-one into a pharmaceutically acceptable salt.

EXAMPLE 1

2-Methyl-5,6,7,8-tetrahydro-2H-1-benzopyran-5-one

A solution of crotonaldehyde (72.74 g, 1.04 mol) in 500 mL of pyridine was added to 1,3-cyclohexanedione (100 g, 0.892 mol) in 500 mL of pyridine and the mixture was heated to reflux under a nitrogen atmosphere for 1 hour. The mixture was cooled to room temperature and then filtered through magnesium sulfate (328 g). The filtrate was concentrated to dryness and the residue was partitioned between water and diethyl ether. The aqueous phase was extracted with diethyl ether and the combined diethyl ether layers were washed with 10% hydrochloric acid (3×150 mL). The diethyl ether layer was then washed with water to neutrality, dried (MgSO$_4$), filtered and the filtrate concentrated to dryness. The residue was purified by Kugelrohr distillation (bp 109°–112° C. (1 to 2 mm)) to give 2-methyl-5,6,7,8-tetrahydro-2H-1-benzopyran-5-one (48.2 g, 0.294 mol) as an oil.

EXAMPLE 2

Ethyl 5-oxo-5,6,7,8-tetrahydro-1-naphthoic acid ester

A mixture of 2-methyl-5,6,7,8-tetrahydro-2H-1-benzopyran-5-one (48.2 g, 0.294 mol), prepared as in Example 1, and 144 mL of ethyl propiolate was heated at 115° C. for approximately 144 hours and then concentrated/n vacuo. The residue was purified by column chromatography over silica gel eluting with mixtures of ethyl acetate and hexane to give 5-oxo-5,6,7,8-tetrahydro-1-naphthoic acid ester (30.68 g, 0.141 mol), m.p. 39°–41° C.

EXAMPLE 3

Ethyl 5-tert-butyldiphenylsiloxy-5,6,7,8-tetrahydro-1-naphthoic acid ester

A mixture of ethyl 5-oxo-5,6,7,8-tetrahydro-1-naphthoic acid ester (30.67 g, 0.141 mol), prepared as in Example 2, and sodium borohydride (6 g) in 500 mL of ethanol was stirred at 0° C. for 1.5 hours. The mixture was concentrated by evaporation and the residue was dissolved in ethyl acetate. The ethyl acetate solution was washed with water, dilute hydrochloric acid, sodium bicarbonate, water and then brine and dried (NaSO$_4$). Concentration by evaporation gave ethyl 5-hydroxy-5,6,7,8-tetrahydro-1-naphthoic acid ester (30.3 g, 0.138 mol) as an oil.

A mixture of ethyl 5-hydroxy-5,6,7,8-tetrahydro-1-naphthoic acid ester (30.3 g, 0.138 mol) tert-butylchlorodiphenylsilane (45.4 g, 0.165 mol) and imidazole (13.7 g, 0.201 mol) in 429 mL of DMF was stirred at room temperature for approximately 24 hours. The mixture was poured into water and extracted with ethyl acetate (2×500 mL). The ethyl acetate layer was washed with water and then brine, dried (NaSO$_4$), filtered and concentrated by evaporation. The residue was purified by column chromatography over silica gel elating with mixtures of ethyl acetate and hexane to give ethyl 5-tert-butyldiphenylsiloxy-5,6,7,8-tetrahydro-1-naphthoic acid ester (63.3 g, 0.138 mol).

EXAMPLE 4

N-(1'-Azabicyclo[2.2.2]oct-3'S-yl)-5-tert-butyldiphenylsiloxy-5,6,7,8-tetrahydro-1-naphthalenecarboxamide A mixture of (S)-1-azabicyclo[2.2.2]oct-3-ylamine (10.43 g, 0.083 mol) and trimethylaluminium (41 mL, 2.0M in toluene, 0.082 mol) in 250 mL of toluene was stirred under a nitrogen atmosphere at room temperature for 0.5 hours. Ethyl 5-tert-butyldiphenylsiloxy-5,6,7,8-tetrahydro-1-naphthoic acid ester (31 g, 0.068 mol), prepared as in Example 3, in 110 mL of toluene was added and the mixture was heated at 110° C. for 48 hours. The mixture was cooled to 0° C. and then 30 mL of water was added. The mixture was stirred at room temperature for 1 hour and then filtered. The filtrate was concentrated and the residue was crystallized from ethyl acetate. The crystalline product was dried under a nitrogen stream to give N-(1'-azabicyclo[2.2.2]oct-3'S-yl)-5-tert-butyldiphenylsiloxy-5,6,7,8-tetrahydro-1- naphthalenecarboxamide (40.8 g, 0.078 mol), m.p. 164°–166° C.

EXAMPLE 5

2-(1'-Azabicyclo[2.2.2]oct-3'S-yl)-6-hydroxy-2,4,5,6-tetrahydro-1H-benz[de] isoquinolin-1-one A solution of N-(1'-azabicyclo[2.2.2]oct-3'S-yl)-5-tert-butyldiphenylsiloxy-5,6,7,8-tetrahydro-1- naphthalenecarboxamide (10 g, 0.019 mol), prepared as in Example 4, in 400 mL of THF was cooled under a nitrogen atmosphere to −70° C. and then sec-butyllithium (70 mL, 1.3M in cyclohexane, 0.091 mol) was slowly added such that the temperature of the reaction mixture remained below −65° C. The mixture was stirred for 10 minutes and then N,N-dimethylformamide (8 mL, 0.103 mol) was added. The mixture was allowed to warm to room temperature and stirred for 0.5 hours. The mixture was then cooled to 0° C., acidified with 200 mL of 10% hydrochloric acid and then stirred at room temperature for 2 hours. The solvents were removed by evaporation and the residue was basified with sodium hydroxide. The basified mixture was extracted with ethyl acetate (4×250 mL). The combined ethyl acetate was washed with brine, dried (MgSO$_4$), filtered and then concentrated to dryness. Purification of the residue by column chromatography over silica gel elating with mixtures of methanol and methylene chloride with a trace amount of ammonium hydroxide gave 2-(1'-azabicyclo[2.2.2]oct-3'S-yl)-6-tert-butyldiphenylsiloxy-2,4,5,6-tetrahydro-1H-benz [de]isoquinolin-1-one (3.8 g, 6.9 mmol).

A mixture of 2-(1'-azabicyclo[2.2.2]oct-3'S-yl)-6-tert-butyldiphenylsiloxy-2,4,5,6-tetrahydro-1H-benz [de]isoquinolin-1-one (3.8 g, 6.9 mmol), and tetrabutylammonium fluoride (12 mL, 1M in THF, 12 mmol) was stirred at room temperature for approximately 24 hours. The solvent was removed by evaporation and the residue was basified. The basified mixture was extracted with ethyl acetate (6×100 mL). The combined ethyl acetate was washed with brine, dried (MgSO$_4$), filtered and then concentrated. The residue was crystallized from methanolic hydrogen chloride to give a diastereomeric mixture of 2-(1'-azabicyclo[2.2.2]oct-3'S-yl)-6R-hydroxy-2,4,5,6-tetrahydro-1H-benz [de]isoquinolin-1-one hydrochloride and 2-(1'-azabicyclo[2.2.2]oct-3'S-yl)-6S-hydroxy-2,4,5,6-tetrahydro-1H-benz [de] isoquinolin-1-one hydrochloride (1.2 g, 3.9 mmol).

EXAMPLE 6

2-(1'-Azabicyclo[2.2.2]oct-3'S-yl)-6R-hydroxy-2,4,5,6-tetrahydro-1H-benz [de]isoquinolin-1-one
and 2-(1'-azabicyclo[2.2.2]oct-3'S-yl)-6S-hydroxy-2,4,5,6-tetrahydro-1H-benz [de]isoquinolin-1-one A diastereomeric mixture of 2-(1'-azabicyclo[2.2.2]oct-3'S-yl)-6R-hydroxy-2,4,5,6-tetrahydro-1H-benz [de]isoquinolin-1-one and 2-(1'-azabicyclo[2.2.2]oct-3'S-yl)-6S-hydroxy-2,4,5,6-tetrahydro-1H-benz [de]isoquinolin-1-one (2.3 g, 7.48 mmol), prepared as in Example 5, was converted to non-salt form and then separated into individual diastereomers by silica gel column gel chromatography elating with 1% ammonium hydroxide/10% methanol/methylene chloride. The more polar diastereomer was isolated to give 2-(1'-azabicyclo[2.2.2]oct-3'S-yl)-6R-hydroxy-2,4,5,6-tetrahydro-1H-benz [de]isoquinolin-1-one (0.55 g, 1.79 mmol), m.p. 205°–206° C.

The less polar diastereomer was isolated to give 2-(1'-azabicyclo[2.2.2]oct-3'S-yl)-6S-hydroxy-2,4,5,6-tetrahydro-1H-benz [de]isoquinolin-1-one (0.48 g, 1.55 mmol), m.p. 205°–206° C.

EXAMPLE 7

2-(1'-Azabicyclo[2.2.2]oct-3'S-yl)-6R-hydroxy-2,3,3aR,4,5,6-hexahydro-1H-benz [de]isoquinolin-1-one and 2-(1'-azabicyclo[2.2.2]oct-3'S-yl)-6R-hydroxy-2,3,3aS,4,5,6-hexahydro-1H-benz [de]isoquinoline-1-one A mixture of 2-(1'-azabicyclo[2.2.2]oct-3'S-yl)-6R-hydroxy-2,4,5,6-tetrahydro-1H-benz [de]isoquinolin-1-one (0.55 g, 1.79 mmol), prepared as in Example 5, and 5% Pd/BaSO$_4$ (0.5 g) in 3 mL of ethanol was stirred under a hydrogen atmosphere at room temperature for approximately 78 hours. The mixture was filtered through Celite and the filter was washed with ethanol. Concentration of the filtrate by evaporation gave a diastereomeric mixture of 2-(1'-azabicyclo[2.2.2]oct-3'S-yl)-6R-hydroxy-2,3,3aS,4,5,6-hexahydro-H-benz [de]isoquinolin-1-one and 2-(1'-azabicyclo[2.2.2]oct-3'S-yl)-6R-hydroxy-2,3,3aR,4,5,6-hexahydro-1H-benz [de]isoquinolin-1-one as an oil.

The diastereomers were separated by silica gel column gel chromatography elating with 1% ammonium hydroxide/ 10% methanol/methylene chloride. The more polar diastereomer was isolated to give 2-(1'-azabicyclo[2.2.2]oct-3'S-yl)-6R-hydroxy-2,3,3aS,4,5,6-hexahydro-1H-benz [de] isoquinolin-1-one (83.8 mg, 0.27 mmol) as an oil. $^1$H NMR (CDCl$_3$): δ 7.99 (1H,d), 7.52 (1H,dd), 7.37 (1H,t), 4.85 (1H,bs), 4.77 (1H,bt), 3.65 (1H,dd), 3.35 (1H,dd), 3.38 (1H,dd), 2.7–3.2 (6H,m), 1.98 (1H,bs), 1.6–2.4 (9H,m).

The less polar diastereomer was isolated to give 2-(1'-azabicyclo[2.2.2]oct-3'S-yl)-6R-hydroxy-2,3,3aR,4,5,6-hexahydro-H-benz [de]isoquinolin-1-one (37.2 mg, 0.12 mmol) as an oil. $^1$H NMR (CDCl$_3$): δ 7.95 (1H,d), 7.45 (1H,t), 7.74 (1H,dd), 4.65–4.9 (2H,m), 3.6 (1H,dd), 3.2 (1H,m), 2.8–3.4 (7H,m), 2.05 (1H,m), 1.4–2.5 (9H,m).

EXAMPLE 8

FORMULATIONS

The following are representative pharmaceutical formulations containing a compound of Formula I.

ORAL FORMULATION

A representative solution for oral administration contains:

| | |
|---|---|
| Compound of Formula I | 100–1000 mg |
| Citric Acid Monohydrate | 105 mg |
| Sodium Hydroxide | 18 mg |
| Flavoring | q.s. |
| Water | to 100 ml |

INTRAVENOUS FORMULATION

A representative solution for intravenous administration contains:

| | |
|---|---|
| Compound of Formula I | 10–100 mg |
| Dextrose Monohydrate | q.s to make isotonic |
| Citric Acid Monohydrate | 1.05 mg |
| Sodium Hydroxide | 0.18 mg |
| Water for Injection | to 1.0 ml |

TABLET FORMULATION

A representative tablet form of a compound of Formula I may contain:

| | |
|---|---|
| Compound of Formula I | 1% |
| Microcrystalline cellulose | 73% |
| Stearic Acid | 25% |
| Colloidal Silica | 1% |

EXAMPLE 9

5-HT$_3$ RECEPTOR BINDING ASSAY

The following describes an in vitro assay for determining the 5-HT$_3$ receptor binding affinity of compounds of Formula I. The method measures the affinity for 5-HT$_3$ receptors of NG 108-15 cell membranes radiolabelled with [$^3$H] granieetron.

NG 108-15 cells were seeded in 225 cm$^2$ tissue culture flasks containing 25 mL of Dulbecco's Modified Eagle's medium supplemented with 10% bovine calf serum and 1× hypoxanthine-aminopterin-thymidine. The cells were incubated at 37° C. in 10% carbon dioxide for three days and then fed. The cells then were incubated at 37° C. for an additional 6 to 7 days and passed every 3 to 4 days thereafter. The media was poured off and the cells were detached from each flask surface by exposing to 5 mL of trypsin for approximately 1 minute while gently tapping the flask on a flat surface. The cell mixture was combined with 30 mL of culture media and the mixture was vortexed and centrifuged (200 ×g for 5 minutes to give a cell pellet. The supernatant was poured off and the cell pellet was suspended in 2 to 3 mL of culture media and pipetted into cryovials. The cell suspensions were stored in liquid nitrogen until required.

NG 108-15 cells from confluent 225 cm$^2$ tissue culture flasks were suspended in 20 volumes (w/v) of an homogenizing buffer (Tris, 50 mM; Na$_2$EDTA, 5 mM). The cells were homogenized with a Polytron P10 tissue disrupter (setting 5, 2×10 sec). The homogenate was centrifuged for 15 minutes at 19,500 rpm in an RC5C centrifuge with an SS34 rotor (300,000-48,000 g). The pellet was suspended in the original volume of homogenizing buffer with a Polytron P10 disrupter (setting 5, 5 sec) and the suspension was centrifuged for 15 minutes at 19,500 rpm in an RC5C centrifuge with an SS34 rotor (300,000-48,000 g). The pellet was resuspended in the original volume of a resuspending buffer (Tris, 50 mM; EDTA 0.5 mM) and the suspension was centrifuged for 15 minutes at 19,500 rpm in an RC5C centrifuge with an SS34 rotor (300,000-48,000 g).

The pellet was resuspended in a small volume of an assay buffer (NaCl, 118 mM; KCl, 4.5 mM; KH$_2$PO$_4$, 1.2 mM; CaCl$_2$·2H$_2$O, 2.5 mM; MgCl$_2$, 1 mM; D-glucose, 10 mM; Tris, 25 mM) with a Polytron P10 disrupter (setting 5, 5 sec). The membrane suspension was separated into 1 mL aliquots and stored under liquid nitrogen until required.

Frozen NG 108-15 cell membranes in 1 mL aliquots were thawed at room temperature and then diluted with assay buffer (an optimal dilution ratio was determined for each batch of membranes to ensure that less than 20% of the [$^3$H]granisetron binds, specific binding is at least 10 times greater than a machine background of 23 dpm and the best ratio of specific binding to total binding is achieved). The membranes were homogenized with a Polytron P10 tissue disrupter (setting 5, 5 sec) and the 5-HT$_3$ receptors present in NG 108-15 cell membranes were labelled with 0.9–1.1 nM [$^3$H]granisetron (specific activity 84.5 Ci/mmol; New England Nuclear). The radiolabelled cell membranes were incubated in the presence of $1\times10^{-11}$–$1\times10^{-5}$M concentrations of test drug at 25° C. in a final volume of 0.25 mL for 45 minutes and then the assay mixture was filtered over 0.3% polyethyleneimine pretreated glass fiber filtermats using a Brandel cell harvester. The assay tubes were rinsed with cold 0.1M sodium chloride (3×8 sec) and dried by drawing air over the filter for 10 seconds. Radioactivity retained on the filters were determined by liquid scintillation counting. In a similar fashion, total binding was measured in the absence of test drug. Zacopride (0.1 μM) was used to define the non-specific binding. For each drug tested the concentration producing 50% inhibition of binding (IC$_{50}$) was determined using iterative curve fitting techniques.

Proceeding as in Example 9, compounds of the invention were tested and found to have affinity for the 5-HT$_3$ receptor.

EXAMPLE 10

5-HT$_3$ RECEPTOR ANTAGONIST ASSAY (VON BEZOLD-JARISCH REFLEX)

The following describes an in vivo assay for determining the 5-HT$_3$ receptor antagonist activity of the compounds of Formula I.

Male Sprague-Dawley rats (250–380 grams) are anesthetized with urethane (1.4 g/kg, i.p.). A tracheotomy is performed and a tube is inserted into the trachea to facilitate respiration. Jugular and femoral veins are cannulated for intravenous administration of drug. The duodenum is cannulated for intraduodenal administration of drug. Heart rate is monitored by Gold ECG/Biotech amplifiers. After at least a 30 minute equilibration period and prior to administration of test compound, control responses to intravenous administration of 2-methyl-5-hydroxytryptamine (2-M-5-HT) are determined and a minimal dose producing sufficient and consistent bradycardia is chosen.

Intravenous challenges to 2-M-5-HT are administered every 12 minutes. Either vehicle or test compound is administered intravenously 5 minutes before each challenge with 2-M-5-HT. Responses to 2-M-5-HT are represented by the peak decrease in heart rate. Each successive administration of test compound is increased in dosage until responses to 2-M-5-HT are blocked. From a dose-response curve so constructed, the concentration of the test compound necessary to produce 50% inhibition of the response induced by 2-M-5-HT is obtained.

EXAMPLE 11

FERRET, ANTI-EMESIS ASSAY

The following describes the procedure for determining the intravenous (i.v.) effects of compounds of Formula I on cisplatin-induced emesis in ferrets.

Adult, male, castrated ferrets are allowed food and water ad libitum both prior to and throughout the testing period. Each animal is randomly chosen and anesthetized with a metofane/oxygen mixture, weighed and assigned to one of three test groups. While anesthetized an incision is made along the ventral cervical region approximately two to four centimeters in length. The jugular vein is then isolated and cannulated with a capped saline filled PE-50 polyethylene tubing. The cannula is exteriorized at the base of the skull and the incision closed with wound clips. The animals are then returned to their cages and allowed to recover from anesthesia prior to commencement of the study.

Vehicle or test compound is administered i.v. at 1.0 ml/kg and 1.0 mg/kg, respectively. Within 2.0 minutes of the administration of vehicle or test compound, cieplatin is injected i.v. at 10 mg/kg. The animals are then observed continuously for a 5 hour period and emetic responses (i.e., vomiting and/or retching) are recorded. For purposes of this example and that of Example 13, vomiting is defined as the successful evacuation of stomach contents and a single episode of retching is defined as rapid and successive efforts to vomit occurring within a one minute time period.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

Proceeding as in Example 12 but administering the test compounds by oral route, the anti-emetic effects of compounds of Formula I may be evaluated.

EXAMPLE 12

DOG, El-EMESIS ASSAY

The following describes the procedure for determining the intravenous (i.v.) effects of compounds of Formula I on cisplatin-induced emesis in dogs.

Male and female dogs (6–15 kg) are fed one cup of dry dog food. One hour following feeding, cisplatin (cis-diamminedichloroplatinum) is administered i.v. at 3 mg/kg. Sixty minutes after the administration of cisplatin, either vehicle or test compound is injected i.v. at 0.1 ml/kg and 1.0 mg/kg, respectively. The dogs are then observed continuously for a 5 hour period and the emetic responses (i.e., vomiting and/or retching) are recorded.

Emetic responses are represented as (1) time to onset of emesis, (2) total vomiting episodes and (3) total retching episodes. Means and standard deviations of the test groups are compared to those of the reference groups. Significance is determined by Student's t-test when comparing a single treatment group to the vehicle control or by Dunnett's comparative analysis when more than one treatment group is compared to a single vehicle.

EXAMPLE 13

PROKINETIC ASSAY

The following describes an in vivo method of determining prokinetic activity by measuring the extent the drug affects the rate of gastric emptying of test meal in rats. The method is that described by Droppleman et al., previously cited.

Test meal is prepared by slowly adding 20 g of cellulose gum (Hercules Inc., Wilmington, Del.) to 200 mL of cold distilled water that is being mixed in a Waring blender at approximately 20,000 rpm. Mixing continues until complete dispersion and hydration of the cellulose gum takes place (approximately 5 min). Three beef bouillon cubes are dissolved in 100 mL of warm water and then blended into the cellulose solution followed by 16 g of purified casein (Sigma Chemical Co., St. Louis, Mo.), 8 g of powdered confectioners sugar, 8 g of cornstarch, and 1 g of powdered charcoal. Each ingredient is added slowly and mixed thoroughly resulting in approximately 325 mL of a dark gray to black, homogenous paste. The meal is then refrigerated overnight during which time trapped air escapes. Prior to the assay the meal is removed from the refrigerator and allowed to warm to room temperature.

Mature (170 to 204 g) male Sprague-Dawley rats are deprived of food for 24 hours with water ad libitum. On the morning of the study each animal is weighed and randomly assigned to treatment groups consisting of ten animals per group. Each rat receives either vehicle, test compound or the reference standard metoclopramide by intraperitoneal injection. At 0.5 hours post injection 3.0 mL of test meal is orally administered to each rat with a 5.0 mL disposable syringe. Five test meal samples are weighed on an analytical balance and these weights are averaged to find a mean test meal weight. At 1.5 hours post injection each rat is sacrificed by carbon dioxide asphyxiation and the stomach is removed by opening the abdomen and carefully clamping and cutting the esophagus just below the pyloric sphincter. Taking care not to lose any of the its contents, each stomach is placed on a small, pre-weighed and correspondingly labeled 7 mL weigh boat and immediately weighed on an analytical balance. Each stomach is then cut open along the lesser curvature, rinsed with tap water, gently blotted dry to remove excess moisture and weighed. The amount of test meal remaining in the stomach is represented by the difference between the weight of the full stomach and the weight of the stomach empty. The difference between the amount of test meal remaining and the mean test meal weight represents the quantity of test meal that empties during the 1.5 hour post injection period.

Responses are represented as grams of meal emptied or percent change from control. Means and standard deviations of the test groups are compared to those of the reference groups. Significance is determined via Dunnett's t-test (Statistical Association Journal, December 1955, 1096-112).

EXAMPLE 14

ANXIOLYTIC BEHAVIOR ASSAY

The following describes an in vivo method for determining anxiolytic activity by measuring the extent the drug affects the natural anxiety of mice when exposed to a novel, brightly lighted environment.

Naive male C5Bl/6J mice, 18–20 g, are kept in groups of 10 mice in quarters controlled for sound, temperature and humidity. Food and water are available ad libitum. The mice are kept on a 12 hour light and 12 hour dark cycle, with lights on at 6:00 a.m. and off at 6:00 p.m. All experiments begin at least 7 days after arrival on site.

The automated apparatus for detecting changes in exploration is obtained from Omni-Tech Electronics Columbus Ohio and is similar to that of Crawley and Goodwin (1980), as described in Kilfoil etal., cited previously. Briefly, the chamber consists of a plexiglass box (44×21×21 cm), divided into two chambers by a black plexiglass partition. The partition dividing the two chambers contains a 13×5 cm opening through which the mouse can easily pass. The dark chamber has clear sides and a white floor. A fluorescent tube light (40 watt) placed above the chambers provides the only illumination. The Digiscan Animal Activity Monitor System RXYZCM16 (Omni-Tech Electronics) records the exploratory activity of the mice within the test chambers.

Prior to commencement of the study the mice are given 60 min to acclimatize to the laboratory environment. After a mouse receives an intraperitoneal (i.p.) injection of either test compound or vehicle it is returned to its home cage for a 15 min post-treatment period. The mouse is then placed in the center of the light chamber and monitored for 10 minutes.

Anxiolysis is seen as a general increase in exploratory activity in the lighted area. An increase in exploratory activity is reflected by increased latency (the time for the mouse to move to the dark chamber when first placed in the center of the lighted area), increase in shuttle activity, increased or unaltered locomotor activity (number of grid lines crossed) and decreased time spent in the dark compartment.

EXAMPLE 15

WITHDRAWAL ANXIETY ASSAY

The following describes an in vivo procedure for determining amelioration of the symptoms caused by withdrawal from addictlye substances by measuring the extent the drug affects the anxiety that occurs in mice after chronically treating with an addictlye substance and then abruptly ceasing the treatments.

Naive male BKW mice (25–30 g) are caged in groups of ten in quarters controlled for sound, temperature and humidity. Food and water are available ad libitum. The mice are kept on a 12 hour light cycle and 12 hour dark cycle, with lights on at 6:00 a.m. and off at 6:00 p.m. All experiments begin at least 7 days after arrival on site.

Levels of anxiety are determined by the two-compartment exploratory model of Crawley and Goodwin (see Example 14). Anxiolysis is seen as a general increase in exploratory activity in the lighted area. An increase in exploratory activity is reflected by increased latency (the time for the mouse to move to the dark chamber when first placed in the center of the lighted area), increased or unaltered locomotor activity (number of grid lines crossed), increased number of rears and decreased time spent in the dark compartment.

Increased exploratory activity in the lighted area is induced by treating the mice for 14 days with ethanol (8.0% w/v in drinking water), nicotine (0.1 mg/kg, i.p., twice daily) or cocaine (1.0 mg/kg, i.p., twice daily). Anxiolysis is assessed 1, 3, 7 and 14 days after commencement of the drug regime. The treatment is abruptly ceased and exploratory activity in the lighted area is determined 8, 24 and 48 hours thereafter. Vehicle or test compounds are administered during the withdrawal phase by intraperitoneal injection. Responses are represented as inhibition of the decrease in anxiolytic behavior after the ethanol, cocaine or nicotine treatment is ceased.

EXAMPLE 16

COGNITIVE ENHANCEMENT ASSAY

The following describes a model to determine the cognitive enhancing activity by measuring the extent the test compound could alleviate the cognitive deficit induced by attopine (30 mg/kg, i.p.) using the Morris Water Maze.

Sprague Dawley rats (240–260 g) were kept in the laboratory the night prior to testing, and remained there throughout the experiment. The Morris Water Maze consists of a circular pool made from black plexiglass (122 cm diameter, 46 cm in height, with a 15 cm rim), filled with opaque water to a height of 35 cm. A hidden platform consisting of black plexiglass was placed 1–2 cm below the surface of the water. The pool was divided into four quadrants, arbitrarily corresponding to north, south, east and west. The platform was located in the south quadrant, about 24 cm from the side. Objects of high contrast were placed about the room to serve as spatial cues. A TV camera tracked the swim path of the rats, and the data thus obtained was examined to determine the time in seconds the rats took to find the platform (escape latency). Test trials were initiated by placing a rat into one of the four quadrants, facing the wall. Testing consisted of a block of six trials (starting first in the north quadrant, then east, south, west, north, and finally east) on each of two consecutive days. During each trial the rat was allowed 90 seconds to find the platform. When the rat successfully found the platform, it was given 30 seconds to "study" the spatial cues. When the rat failed to find the platform within 90 seconds, it was given a score of 90 seconds, and placed on the platform for 30 seconds.

The following groups of 8 rats each were used: 1) vehicle-treated controls; 2) atropine treated-controls; 3) attopine plus test drug. Thus the studies were designed to determine whether the test drug could alleviate the cognitive deficit induced by attopine (30 mg/kg, i.p.). Statistical tests were applied to test for heterogeneity of the learning curves, and separation of the learning curves.

While the present invention has been described with respect to specific embodiments thereof, it will be understood by those skilled in the art that various changes may be made and equivalents may be substituted without departing from the true spirit and scope of the invention. All such modifications are intended to be within the scope of the claims appended hereto.

We claim:

1. A compound of Formula I:

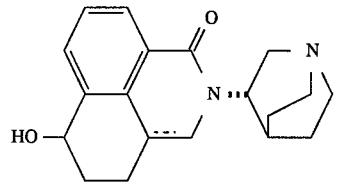

in which the dashed line denotes an optional double bond; and the pharmaceutically acceptable salts, individual stereoisomers, mixtures of isomers, N-oxide derivatives and O-β-D-glucuronide conjugates thereof.

2. The compound of claim 1 in which the optional bond is not present, namely 2-(1'-azabicyclo[2.2.2]oct-3'S-yl)-6-hydroxy-2,3,3a,4,5,6-hexahydro-1H-benz [de]isoquinolin-1-one or a pharmaceutically acceptable salt thereof.

3. The compound of claim 2 which is 2-(1'-azabicyclo [2.2.2]oct-3'S-yl)-6R-hydroxy-2,3,3aS,4,5,6-hexahydro-1H-benz [de]isoquinolin-1-one or a pharmaceutically acceptable salt thereof.

4. The compound of claim 3 which is 2-(1'-azabicyclo [2.2.2]oct-3'S-yl)-6R-hydroxy-2,3,3aS,4,5,6-hexahydro-1H-benz [de]isoquinolin-1-one hydrochloride.

5. The compound of claim 2 which is 2-(1'-azabicyclo [2.2.2]oct-3'S-yl)-6S-hydroxy-2,3,3aS,4,5,6-hexahydro-1H-benz [de]isoquinolin-1-one or a pharmaceutically acceptable salt thereof.

6. The compound of claim 5 which is 2-(1'-azabicyclo [2.2.2]oct-3'S-yl)-6S-hydroxy-2,3,3aS,4,5,6-hexahydro-1H-benz [de]isoquinolin-1-one hydrochloride.

7. The compound of claim 2 which is 2-(1'-azabicyclo [2.2.2]oct-3'S-yl)-6R-hydroxy-2,3,3aR,4,5,6-hexahydro-1H-benz [de]isoquinolin-1-one or a pharmaceutically acceptable salt thereof.

8. The compound of claim 7 which is 2-(1'-azabicyclo [2.2.2]oct-3'S-yl)-6R-hydroxy-2,3,3aR,4,5,6-hexahydro-1H-benz [de]isoquinolin-1-one hydrochloride.

9. The compound of claim 2 which is 2-(1'-azabicyclo [2.2.2]oct-3'S-yl)-6S-hydroxy-2,3,3aR,4,5,6-hexahydro-1H-benz [de]isoquinolin-1-one or a pharmaceutically acceptable salt thereof.

10. The compound of claim 9 which is 2-(1'-azabicyclo [2.2.2]oct-3'S-yl)-6S-hydroxy-2,3,3aR,4,5,6-hexahydro-1H-benz [de]isoquinolin-1-one hydrochloride.

11. The compound of claim 1 in which the optional bond is present, namely 2-(1'-azabicyclo[2.2.2]oct-3'S-yl)-6-hydroxy-2,4,5,6-tetrahydro-1H-benz [de]isoquinolin-1-one or a pharmaceutically acceptable salt thereof.

12. The compound of claim 11 which is 2-(1'-azabicyclo [2.2.2]oct-3'S-yl)-6R-hydroxy-2,4,5,6-tetrahydro-1H-benz [de]isoquinolin-1-one or a pharmaceutically acceptable salt thereof.

13. The compound of claim 12 which is 2-(1'-azabicyclo [2.2.2]oct-3'S-yl)-6R-hydroxy-2,4,5,6-tetrahydro-1H-benz [de] isoquinolin-1-one hydrochloride.

14. The compound of claim 11 which is 2-(1'-azabicyclo [2.2.2]oct-3'S-yl)-6S-hydroxy-2,4,5,6-tetrahydro-1H-benz [de] isoquinolin-1-one or a pharmaceutically acceptable salt thereof.

15. The compound of claim 14 which is 2-(1'-azabicyclo [2.2.2]oct-3'S-yl)-6S-hydroxy-2,4,5,6-tetrahydro-1H-benz [de] isoquinolin-1-one hydrochloride.

16. A pharmaceutical composition comprising a therapeutically effective amount of a compound of claim 1 in combination with a pharmaceutically acceptable excipient.

17. A method for treating a condition chosen from emesis, a gastro-intestinal disorder treatable with prokinetic agents, a cognitive disorder, psychosis, anxiety/depressive state, obsessive/compulsive behavior, hypertension, arrhythmia and pain in an animal in need of such treatment, which method comprises administering a therapeutically effective amount of a compound of Formula I:

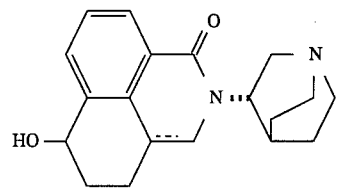

in which the dashed line denotes an optional double bond; or a pharmaceutically acceptable salt, individual stereoisomer, mixture of stereoisomers, N-oxide derivative or O-β-D-glucuronide conjugate thereof.

18. The method of claim 17 in which the condition is a gastrointestinal disorder treatable with a prokinetic agent.

19. The method of claim 17 in which the condition is pain.

20. The method of claim 17 in which the condition is anxiety/depressive state.

21. The method of claim 17 in which the condition is the side effects caused by withdrawal from an addictlye substance.

22. The method of claim 17 in which the condition is emesis.

23. The method of claim 22 in which the condition is emesis in humans undergoing cancer treatment with a cytotoxic pharmaceutical agent or radiation at levels sufficient to induce emesis, or recovering from surgical anesthesia or undergoing drug therapy in general in which a significant side effect is emesis.

* * * * *